United States Patent
Snell et al.

(10) Patent No.: US 8,150,529 B2
(45) Date of Patent: Apr. 3, 2012

(54) MEDICAL DEVICES AND SYSTEMS HAVING SEPARATE POWER SOURCES FOR ENABLING DIFFERENT TELEMETRY SYSTEMS

(75) Inventors: Jeffery D. Snell, Chatsworth, CA (US); Gene A. Bornzin, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 1022 days.

(21) Appl. No.: 12/104,301

(22) Filed: Apr. 16, 2008

(65) Prior Publication Data
US 2009/0264950 A1 Oct. 22, 2009

(51) Int. Cl.
*A61N 1/08* (2006.01)

(52) U.S. Cl. ............... 607/60; 607/29; 607/31; 607/32; 607/30; 128/904

(58) Field of Classification Search ............... 607/27, 607/30–32, 60; 128/903, 904
See application file for complete search history.

(56) References Cited

U.S. PATENT DOCUMENTS

| | | | |
|---|---|---|---|
| 4,686,988 A | 8/1987 | Sholder | |
| 4,708,142 A | 11/1987 | DeCote, Jr. | |
| 4,712,555 A | 12/1987 | Thornander et al. | |
| 4,729,376 A | 3/1988 | DeCote, Jr. | |
| 4,788,980 A | 12/1988 | Mann et al. | |
| 4,809,697 A | 3/1989 | Causey, III et al. | |
| 4,940,052 A | 7/1990 | Mann et al. | |
| 4,944,298 A | 7/1990 | Sholder | |
| 4,944,299 A | 7/1990 | Silvian | |
| 4,969,467 A | 11/1990 | Callaghan et al. | |
| 5,350,410 A | 9/1994 | Kleks et al. | |
| 6,275,734 B1 | 8/2001 | McClure et al. | |
| 6,622,043 B1 * | 9/2003 | Kraus et al. | 607/27 |
| 2003/0114898 A1 * | 6/2003 | Von Arx et al. | 607/60 |
| 2003/0114899 A1 * | 6/2003 | Woods et al. | 607/60 |
| 2009/0036943 A1 * | 2/2009 | Signoff et al. | 607/36 |

* cited by examiner

*Primary Examiner* — Carl H Layno
*Assistant Examiner* — Pamela M Bays

(57) ABSTRACT

An implantable medical device includes a first, short-range telemetry circuit; a second, long-range telemetry circuit; a first power system that powers the first telemetry circuit; and a second power system that powers the second telemetry circuit. The second power system includes an internal charging system and a rechargeable battery coupled to the internal charging system. The internal charging system may be configured for electromagnetic-inductive or RF-transmission coupling with an external charging system. A controller monitors the energy level of the rechargeable battery and provides an signal indicative of the level.

10 Claims, 2 Drawing Sheets

MEDICAL DEVICES AND SYSTEMS HAVING SEPARATE POWER SOURCES FOR ENABLING DIFFERENT TELEMETRY SYSTEMS

FIELD OF THE INVENTION

The present invention relates generally to powering medical devices and systems and more particularly to implantable medical devices and medical systems having separate power sources for enabling different telemetry systems.

BACKGROUND OF THE INVENTION

An implantable cardiac device is a medical device that is implanted in a patient to monitor electrical activity of a heart and to deliver appropriate electrical. Implantable cardiac devices include, for example, pacemakers, cardioverters, defibrillators, and the like. The term "implantable cardioverter defibrillator" or simply "ICD" is used hereinafter to refer to any implantable cardiac device.

An ICD employs a battery to power its internal circuitry and to generate electrical therapy for delivery to the patient. The electrical therapy can include any one of pacing pulses, cardioversion pulses or defibrillation pulses. In addition to providing electrical therapy, the ICD generates information related to device operation, patient therapy and patient status. Such information is typically provided to the patient's care provider using a telemetry circuit that communicates with a nearby, short-range external system, such as a device programmer. In conventional ICDs, a single power source provides the power necessary to operate internal circuitry, generate electrical therapy and transmit information.

Communication between ICDs and more remote, long-range external devices is also desirable. Unfortunately, long-range telemetry systems require substantially more power than short-range system, and accordingly may reduce the lifetime of a typical ICD battery. A substantial decrease in battery life is undesirable in that device replacement may be required at an earlier stage.

BRIEF SUMMARY OF THE INVENTION

Briefly, and in general terms the invention is directed to implantable medical devices and medical systems having separate power sources for enabling different telemetry systems. In one aspect, the invention relates to an implantable medical device that includes a first, short-range telemetry circuit; a second, long-range telemetry circuit; a first power system that powers the first telemetry circuit; and a second power system that powers the second telemetry circuit. The second power system may include an internal charging system and a rechargeable battery coupled to the internal charging system. The internal charging system may be configured for electromagnetic-inductive or RF-transmission coupling with an external charging system. A controller monitors the energy level of the second power system and outputs a signal related to the energy level, which may be a warning signal if the energy is below a threshold level or simply a diagnostic signal conveying the current energy level of the second power system.

These and other aspects and advantages of the invention will become apparent from the following detailed description and the accompanying drawings which illustrate by way of example the features of the invention.

DETAILED DESCRIPTION

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designations will be used to refer to like parts or elements throughout.

It would be apparent to one of skill in the art that the present invention, as described below, may be implemented in many different embodiments of hardware, software, and/or firmware. Any actual software and/or hardware described herein is not limiting of the present invention. Thus, the operation and behavior of the present invention will be described with the understanding that modifications and variations of the embodiments are possible, given the level of detail presented herein.

Overview

The present invention includes an implanted medical device having the ability to communicate with both local and remote external receiving devices without unduly limiting the life of a normal power supply to the medical device. The medical device includes a first, low-power consumption, short-range telemetry circuit and a second, high-power consumption, long-range telemetry circuit. A first power system powers the first telemetry circuit and other internal circuitry, such as a microcontroller, switches, sensors and pulse generators. A second power system powers the second telemetry circuit. A controller monitors the second power system to determine when it needs to be recharged, to indicate this to the patient or an external device, and to initiate a recharging operation in conjunction with an external charging system. In this arrangement, the second power system is used for the high-power consumption, long-range second telemetry system, so as not to drain any unnecessary power from the first, low-power, short-range telemetry system.

Before describing the invention in detail, it is helpful to describe an example environment in which the invention may be implemented. The present invention is particularly useful in the environment of an implantable cardiac device (ICD) as described below.

Exemplary ICD in Electrical Communication with a Patient's Heart

Figure 1:
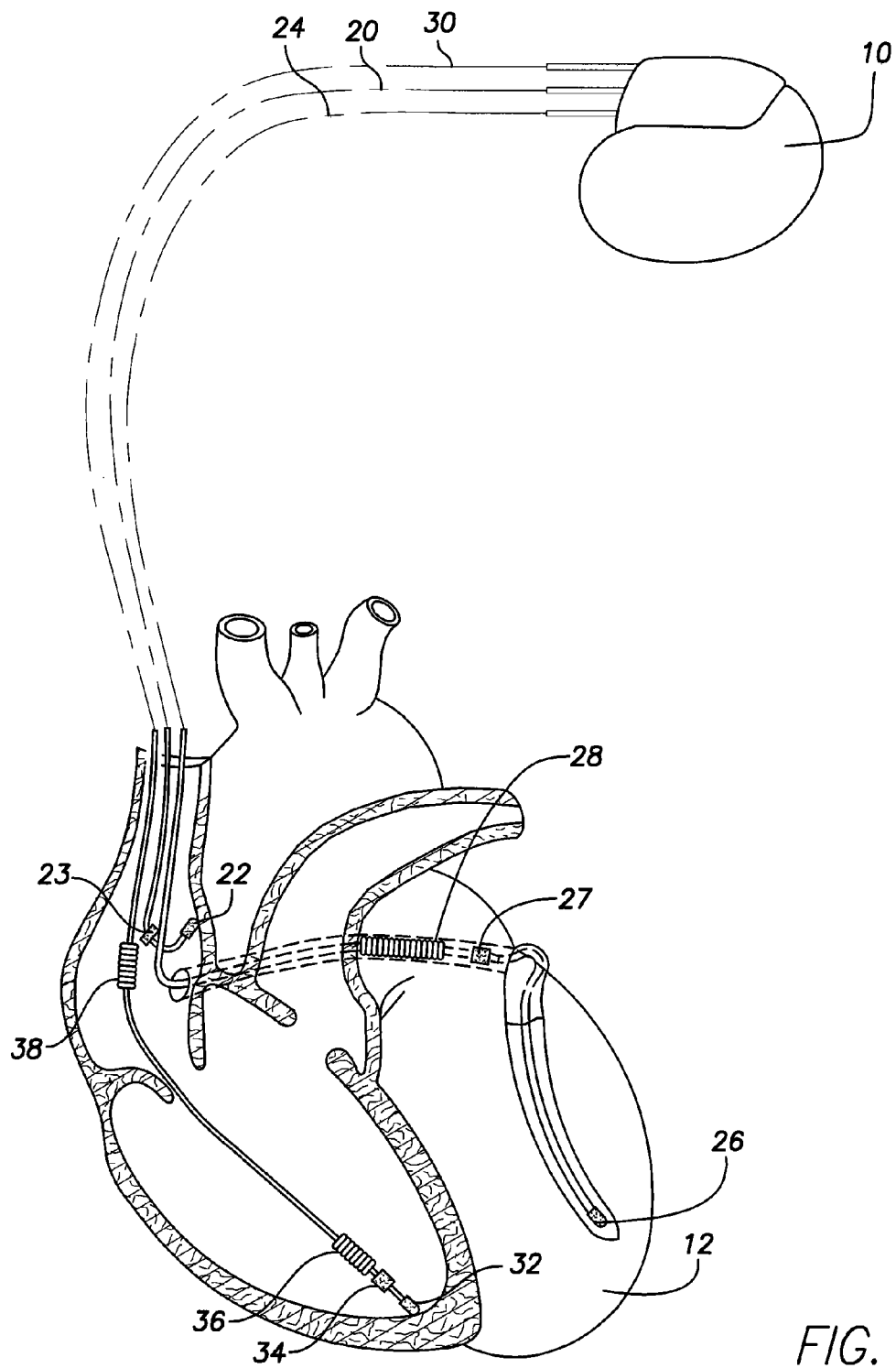
FIG. 1 is a diagram illustrating an ICD in electrical communication with at least three leads implanted into a patient's heart for delivering multi-chamber stimulation and shock therapy according to an embodiment of the present invention.

As shown in FIG. 1, an exemplary ICD 10 is in electrical communication with a patient's heart 12 by way of three leads, 20, 24 and 30, suitable for delivering multi-chamber stimulation and pacing therapy. To sense atrial cardiac signals and to provide right atrial chamber stimulation therapy, the ICD 10 is coupled to an implantable right atrial lead 20 having at least an atrial tip electrode 22, which typically is implanted in the patient's right atrial appendage, and an atrial ring electrode 23.

To sense left atrial and ventricular cardiac signals and to provide left-chamber pacing therapy, the ICD 10 is coupled to coronary sinus lead 24 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The ICD 10 is also shown in electrical communication with the patient's heart 12 by way of an implantable right ventricular lead 30 having a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that RV coil electrode 36 is positioned in the right ventricle and SVC coil electrode 38 is positioned in the superior vena cava. Accordingly, right ventricular lead 30 is capable of receiving cardiac signals and delivering stimulation in the form of pacing and shock therapy to the right ventricle.

Functional Elements of an Exemplary ICD

Figure 2:
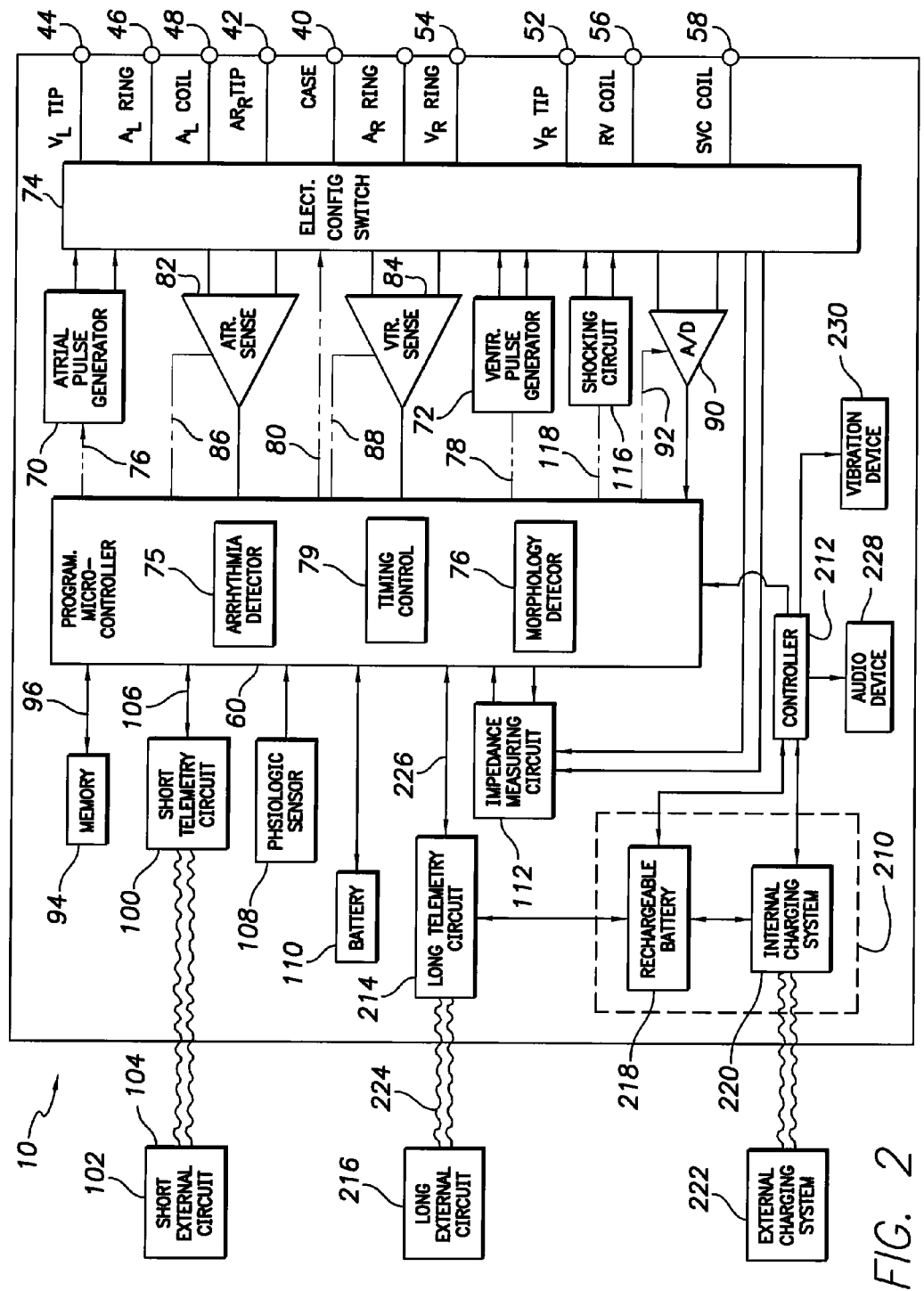
FIG. 2 is a block diagram of an ICD that incorporates the present invention and can provide cardioversion, defibrillation and pacing stimulation in four chambers of a heart according to an embodiment of the present invention.

FIG. 2 shows a block diagram of the ICD 10, which is capable of treating both fast and slow arrhythmias with stimulation therapy, including cardioversion, defibrillation, and pacing stimulation. While a particular multi-chamber stimulation device is shown, it is shown for illustration purposes only, and one of skill in the art could readily duplicate, eliminate or disable the appropriate circuitry in any desired combination to provide a device capable of treating the appropriate chamber(s) with the desired cardioversion, defibrillation and pacing stimulation.

A housing 40 of the ICD 10, shown schematically in FIG. 2, is often referred to as the "can," "case" or "case electrode" and may be programmably selected to act as the return electrode for all "unipolar" modes. The housing 40 may further be used as a return electrode alone or in combination with one or more of the coil electrodes, 28, 36, and 38 for shocking purposes. The housing 40 further includes a connector (not shown) having a plurality of terminals 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22. A right atrial ring terminal ($A_R$ RING) 43 may also be included and adapted for connection to the right atrial ring electrode 23.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to left ventricular tip electrode 26, left atrial tip electrode 27, and left atrial coil electrode 28, respectively.

To support right chamber sensing, pacing, and shocking the connector also includes a right ventricular tip terminal ($V_R$ TIP) 52, a right ventricular ring terminal ($V_R$ RING) 54, a right ventricular shocking terminal (RV COIL) 56, and an SVC shocking terminal (SVC COIL) 58, which are configured for connection to right ventricular tip electrode 32, right ventricular ring electrode 34, RV coil electrode 36, and SVC coil electrode 38, respectively.

At the core of ICD 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design of the microcontroller 60 are not critical to the present invention. Rather, any suitable microcontroller 60 can be used to carry out the functions described herein. The use of microprocessor-based control circuits for performing timing and data analysis functions are well known in the art.

Representative types of control circuitry that may be used with the invention include the microprocessor-based control system of U.S. Pat. No. 4,940,052 (Mann et al.) and the state-machines of U.S. Pat. No. 4,712,555 (Thornander et al.) and U.S. Pat. No. 4,944,298 (Sholder). For a more detailed description of the various timing intervals used within the ICD's and their inter-relationship, see U.S. Pat. No. 4,788, 980 (Mann et al.). The '052, '555, '298 and '980 patents are incorporated herein by reference.

As shown in FIG. 2, an atrial pulse generator 70 and a ventricular pulse generator 72 generate pacing stimulation pulses for delivery by right atrial lead 20, right ventricular lead 30, and/or coronary sinus lead 24 via an electrode configuration switch 74. It is understood that in order to provide stimulation therapy in each of the four chambers of the heart, the atrial and ventricular pulse generators 70 and 72 may include dedicated, independent pulse generators, multiplexed pulse generators, or shared pulse generators. The pulse generators 70 and 72 are controlled by microcontroller 60 via appropriate control signals 76 and 78, respectively, to trigger or inhibit the stimulation pulses.

The microcontroller 60 further includes timing control circuitry 79, which is used to control pacing parameters (e.g., the timing of stimulation pulses) as well as to keep track of the timing of refractory periods, PVARP intervals, noise detection windows, evoked response windows, alert intervals, marker channel timing, etc., which are well known in the art. Examples of pacing parameters include, but are not limited to, atrio-ventricular (AV) delay, interventricular (RV-LV) delay, atrial interconduction (A-A) delay, ventricular interconduction (V-V) delay, and pacing rate.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, the coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits 82, 84 may include dedicated sense amplifiers, multiplexed amplifiers, or shared amplifiers. The switch 74 determines the "sensing polarity" of the cardiac signal by selectively closing the appropriate switches, as is also known in the art. In this way, a clinician may program the sensing polarity independent of the stimulation polarity.

Each sensing circuit 82, 84, preferably employs one or more low power, precision amplifiers with programmable gain and/or automatic gain control, bandpass filtering, and a threshold detection circuit, as known in the art, to selectively sense the cardiac signal of interest. The automatic gain control enables the ICD 10 to deal effectively with the difficult problem of sensing the low amplitude signal characteristics of atrial or ventricular fibrillation. Such sensing circuits 82, 84 can be used to determine cardiac performance values used in the present invention.

The outputs of the atrial and ventricular sensing circuits 82, 84 are connected to the microcontroller 60 which, in turn, is able to trigger or inhibit atrial and ventricular pulse generators 70, 72, respectively, in a demand fashion in response to the absence or presence of cardiac activity, in the appropriate chambers of the heart. The sensing circuits 82, 84, in turn, receive control signals over signal lines 86, 88 from microcontroller 60 for purposes of measuring cardiac performance at appropriate times, and for controlling the gain, threshold, polarization charge removal circuitry (not shown), and timing of any blocking circuitry (not shown) coupled to the inputs of the sensing circuits 82, 86.

For arrhythmia detection, the ICD 10 utilizes the atrial and ventricular sensing circuits 82, 84 to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). The microcontroller 60 utilizes arrhythmia detection circuitry 75 and morphology detection circuitry 76 to recognize and classify arrhythmia so that appropriate therapy can be delivered.

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102, 216. The data acquisition system 90 is coupled to the right atrial lead 20, the coronary sinus lead 24, and the right ventricular lead 30 through the switch 74 to sample cardiac signals across any pair of desired electrodes.

The data acquisition system 90 can be coupled to the microcontroller 60, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via a control signal 92 to sample the cardiac signal that falls in the capture detection window. Based on the amplitude of the cardiac signal within the capture detection window, the microcontroller 60 determines if capture has occurred.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Kleks et al.), which patents are hereby incorporated herein by reference. The type of capture detection system used is not critical to the present invention.

The microcontroller 60 is further coupled to a memory 94 by a suitable data/address bus 96, wherein the programmable operating parameters used by the microcontroller 60 are stored and modified, as required, in order to customize the operation of the ICD 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart within each respective tier of therapy.

The operating parameters of the ICD 10 may be non-invasively programmed into the memory 94 through a short-range telemetry circuit 100 in telemetric communication with short-range external device 102, such as a programmer, transtelephonic transceiver, or a diagnostic system analyzer. The short-range telemetry circuit 100 is activated by the microcontroller 60 by a control signal 106. The telemetry circuit 100 allows intracardiac electrograms and status information relating to the operation of the ICD 10, as contained in the microcontroller 60 or the memory 94, to be sent to the short-range external device 102 through an established communication link 104. Communication link 104 can be wired or wireless depending on a particular application and both are contemplated within the scope of the present invention.

For examples of devices including telemetric communication, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734, entitled "Efficient Generation of Sensing Signals in an Implantable Medical Device such as a Pacemaker or ICD" (McClure et al.), which patents are hereby incorporated herein by reference.

In one embodiment, the ICD 10 further includes a physiologic sensor 108 that can be used to detect changes in cardiac performance or changes in the physiological condition of the heart. Accordingly, the microcontroller 60 can respond by adjusting the various pacing parameters (such as rate, AV Delay, RV-LV Delay, V-V Delay, etc.). The microcontroller 60 controls adjustments of pacing parameters by, for example, controlling the stimulation pulses generated by the atrial and ventricular pulse generators 70, 72. While shown as being included within the ICD 10, it is to be understood that the physiologic sensor 108 may also be external to ICD, yet still be implanted within or carried by the patient. More specifically, the physiologic sensor 108 can be located inside the ICD 10, on the surface of the ICD 10, in a header of the ICD 10, or on a lead (which can be placed inside or outside the bloodstream).

The ICD 10 further includes a magnet detection circuitry (not shown), coupled to the microcontroller 60. The magnet detection circuitry detects the presence of a magnet placed outside the patient's body over the ICD 10. A clinician may use the magnet to perform various test functions of the ICD 10 and/or to signal the microcontroller 60 that an external device 102, such as a programmer, is in place to receive or transmit data to the microcontroller 60 through the telemetry circuit 100.

As further shown in FIG. 2, the ICD 10 includes an impedance measuring circuit 112, which is enabled by the microcontroller 60 via a control signal 114. Known uses for an impedance measuring circuit 112 include, but are not limited to, lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 112 can be coupled to the switch 74 so that any desired electrode may be used. The impedance measuring circuit 112 is not critical to the present invention and is shown only for completeness.

In the case where the ICD 10 is intended to operate as a cardioverter, pacer or defibrillator, it is operative to detect the occurrence of an arrhythmia and automatically apply an appropriate electrical therapy to the heart aimed at terminating the detected arrhythmia. To this end, the microcontroller 60 further controls a shocking circuit 116 by way of a control signal 118. The shocking circuit 116 generates shocking pulses of low (e.g., up to about 0.5 Joules), moderate (about 0.5 to about 10 Joules), or high energy (about 11 to about 40 Joules), as controlled by the microcontroller 60. Such shocking pulses are applied to the patient's heart through at least two shocking electrodes (e.g., selected from the LA coil electrode 28, the RV coil electrode 36, and the SVC coil electrode 38). As noted above, the housing 40 may act as an active electrode in combination with the RV electrode 36, or as part of a split electrical vector using the SVC coil electrode 38 or the LA coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized to be recognized), and pertaining exclusively to the treatment of fibrillation. Accordingly, the microcontroller 60 is capable of controlling the synchronous or asynchronous delivery of the shocking pulses.

The ICD 10 additionally includes a first power system 110 (e.g., a battery), which provides operating power to a load that includes the short-range telemetry circuit 100 and most of the other circuitry within the housing 40. Because the ICD 10 employs shocking therapy, the battery 110 must be capable of operating at low current drains for long periods of time, and then be capable of providing high-current pulses (for capacitor charging) when the patient requires a shock pulse. Because the lower current drains occur over much longer periods of time than the higher current drains, the lower current drains typically account for a significant portion of battery consumption. Elective replacement time of the battery 110 may be determined by monitoring the level of battery depletion. The battery 110 may be a lithium/silver vanadium oxide battery but other battery chemistries can also be used.

The ICD 10 consumes current over a wide dynamic range according to the mode of operation. In one embodiment, the ICD 10 can draw current from the first power system 110 over the range of about 10 μA to 10 mA. For example, the ICD 10 can draw much more than 1 mA for burst pacing or high speed telemetry and 10 μA or less for powering the ICD 10 sensing electronics. Battery current consumption is normally in the μA range for pacemakers with peaks occurring during the generation of the pacing pulses. Other battery functions can draw 10 mA or more from the battery 110 and, for a cardioverter or defibrillator, the capacitor charging current is typically about 3 A. A switched capacitor current integrator (not shown) accurately determines the level of battery depletion by accumulating the total integrated current over a wide dynamic range of current consumed by the ICD 10.

The ICD 10 further includes a second or long-range telemetry circuit 214 that is operative to communicate with a second or long-range external device 216 such as a programmer, transtelephonic transceiver, a diagnostic system analyzer, or the like. The long-range external device may be quite far from the ICD 10. As such, the long-range telemetry circuit 214 generates a signal having a relative large magnitude compared to the signal transmitted from short-range telemetry circuit 100. The long-range telemetry circuit 214 is activated by the microcontroller 60 by a control signal 226. The long-range telemetry circuit 214 can allow intracardiac electrograms and status information relating to the operation of the ICD 10 (as contained in the microcontroller 60 or the memory 94) to be sent to the long-range external device 216 through an established communication link 224. The communication link 224 can be wired or wireless depending on a particular application and both are contemplated within the scope of the present invention.

In accordance with the present invention, the long-range telemetry circuit 214 is powered by a second power system 210 that is separate from the first power system 110. This second power system 210 reduces the load on the first power system 110 and thereby alleviates the first power system from becoming untimely depleted. In one configuration, the second power system 210 includes a rechargeable battery 218 and an internal charging system 220. The internal charging system 220 is coupled, preferably wirelessly, to the external charging system 222. However, wired coupling arrangements are also contemplated within the scope of the present invention.

A controller 212 is coupled to both the rechargeable battery 218 and the internal charging system 220. The controller 212 monitors the rechargeable battery 218 to determine its energy level and to provide a signal related to the energy level. In one configuration, the controller 212 provides a warning signal when the energy level is below a threshold. The controller 212 may also provide a diagnostic signal indicative of the current energy level of the rechargeable battery 218.

In the case of a warning signal, the controller 212 may provide the signal to a patient notifier within the ICD 10, such as an audio device 228 or a vibration device 230, which in response to the signal provides an audible notification or physically detectible vibration notification to the patient. These notifications may serve to indicate, for example, that rechargeable battery 218 needs to be recharged within a certain time period. The controller 212 may also provide the warning signal to one or more of the short-range or long-range external device 102, 216, through their respective short-range or long-range telemetry circuits 100, 214. The external devices 102, 216, in turn, may provide an audible or visual warning indication. In the case of diagnostic signals the controller 212 may provide the signal to the memory 94 for storage and subsequent transmission or it may transmits it directly to one or more of the short-range and long-range external devices 102, 216.

Regarding energy level threshold, there may be several threshold levels that cause an indication signal so that there is ample time for the person with the ICD 10 to recharge rechargeable battery 218. Once alerted, the person can move an external charging system 222 proximate the ICD 10, so that the internal charging system 220 can receive a signal from external charging system. In this regard, the signal can be an electromagnetic signal that is inductively transmitted from a coil in the external charging system 222 to a coil in the internal charging system 220. As another example, the signal can be a radio frequency signal transmitted from a transmitter in external charging system 222 to a receiver in internal charging system 220. For examples of such non-contacting power transferring systems, see U.S. Pat. Nos. 3,942,535, 5,411,537, 5,713,939, 5,733,313, 5,769,877, 6,340,444, 6,456,883, and 6,505,077, which are all incorporated herein by reference in their entireties. It is noted that "external" within the context of this description, means outside the body, while "internal" means within the body. Thus, the recharging operation performed between the external charging system 222 and the internal charging system is transcutaneous in that it involves signals passing through tissue.

CONCLUSION

Example embodiments of the devices and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

What is claimed is:

1. A medical system comprising:
   an implantable medical device having a housing, a short-range telemetry circuit within the housing, a long-range telemetry circuit within the housing, other internal circuitry within the housing, a first power system within the housing that powers the short-range telemetry circuit and the other internal circuitry, and a rechargeable second power system within the housing that powers the long-range telemetry circuit; and
   an external charging system operative to recharge the second power system.

2. The system of claim 1 further comprising an external device configured for coupling with one or both of the short-range telemetry circuit and the long-range telemetry circuit.

3. The system of claim 2 wherein the external device is configured for inductive coupling with the short-range telemetry circuit.

4. The system of claim 2 wherein the external device is configured for RF coupling with the short-range telemetry circuit.

5. The system of claim 2 wherein the external device is configured for RF coupling with the long-range telemetry circuit.

6. The system of claim 2 wherein the implantable medical device further includes a controller configured to monitor the energy level of the second power system and output a signal related to the energy level for transmission to the external device.

7. The device of claim 6 wherein the signal comprises a warning signal when the energy level is below a threshold.

8. The device of claim 6 wherein the signal comprises a diagnostic signal indicative of the energy level.

9. The device of claim 6 wherein the output signal is operative to generate one of an audio, a visual, or a physically detectable indication.

10. The device of claim 6 wherein the output signal is transmitted by one of the first telemetry circuit and the second telemetry circuit to an external device.

* * * * *